(12) United States Patent
Bowen et al.

(10) Patent No.: US 11,647,783 B2
(45) Date of Patent: *May 16, 2023

(54) DEVICES FOR VAPORIZATION OF A SUBSTANCE

(71) Applicant: JUUL Labs, Inc., Washington, DC (US)

(72) Inventors: Adam Bowen, San Mateo, CA (US); James Monsees, San Francisco, CA (US)

(73) Assignee: JUUL Labs, Inc., Washington, DC (US)

( * ) Notice: Subject to any disclaimer, the term of this patent is extended or adjusted under 35 U.S.C. 154(b) by 289 days.

This patent is subject to a terminal disclaimer.

(21) Appl. No.: 16/372,342

(22) Filed: Apr. 1, 2019

(65) Prior Publication Data

US 2019/0289916 A1  Sep. 26, 2019

Related U.S. Application Data

(63) Continuation of application No. 15/165,954, filed on May 26, 2016, now Pat. No. 10,244,793, which is a
(Continued)

(51) Int. Cl.
*A24F 1/32* (2006.01)
*A24F 13/04* (2006.01)
(Continued)

(52) U.S. Cl.
CPC .................. *A24F 1/32* (2013.01); *A24F 7/02* (2013.01); *A24F 13/04* (2013.01); *A24F 40/40* (2020.01);
(Continued)

(58) Field of Classification Search
None
See application file for complete search history.

(56) References Cited

U.S. PATENT DOCUMENTS 720,007 A   2/1903  Dexter
1,165,000 A  12/1915  Dula
(Continued)

FOREIGN PATENT DOCUMENTS

CA   1329098 C   5/1994
CA   2641869 A1  5/2010
(Continued)

OTHER PUBLICATIONS

U.S. Appl. No. 11/485,168, filed Jun. 11, 2006, U.S. Pat. No. 9,675,109.
(Continued)

*Primary Examiner* — Phu H Nguyen
(74) *Attorney, Agent, or Firm* — Mintz Levin Cohn Ferris Glovsky and Popeo, P.C.

(57) ABSTRACT

Devices for generating and releasing vapor. In particular, described herein are portable devices for generating a low-temperature inhalable vapor having an elongated tubular body containing a vaporization chamber and a battery-powered heater, a removable mouthpiece covering the vaporization chamber, a display configured to indicate the temperature of the vaporization chamber; a microcontroller configured to regulate the temperature of the vaporization chamber, and a control to select from among a variety of temperature settings.

18 Claims, 8 Drawing Sheets

Related U.S. Application Data continuation-in-part of application No. 14/578,193, filed on Dec. 19, 2014, now Pat. No. 10,834,964, which is a continuation of application No. 11/485,168, filed on Jul. 11, 2006, now Pat. No. 9,675,109.

(60) Provisional application No. 60/700,105, filed on Jul. 19, 2005.

(51) Int. Cl.
| | |
|---|---|
| *A61M 15/00* | (2006.01) |
| *A61M 15/06* | (2006.01) |
| *F21V 33/00* | (2006.01) |
| *H05B 3/34* | (2006.01) |
| *H05B 3/14* | (2006.01) |
| *H05B 1/02* | (2006.01) |
| *B01B 1/00* | (2006.01) |
| *G05D 23/19* | (2006.01) |
| *A24F 7/02* | (2006.01) |
| *A61M 11/04* | (2006.01) |
| *G06F 3/147* | (2006.01) |
| *A24F 40/40* | (2020.01) |
| *A24F 40/50* | (2020.01) |
| *A24F 40/60* | (2020.01) |
| *F21Y 115/10* | (2016.01) |
| *G06F 3/02* | (2006.01) |
| *A24F 40/20* | (2020.01) |

(52) U.S. Cl.
CPC ............. *A24F 40/50* (2020.01); *A24F 40/60* (2020.01); *A61M 11/042* (2014.02); *A61M 11/048* (2014.02); *A61M 15/0028* (2013.01); *A61M 15/06* (2013.01); *B01B 1/005* (2013.01); *F21V 33/0004* (2013.01); *G05D 23/1917* (2013.01); *G06F 3/147* (2013.01); *H05B 1/0244* (2013.01); *H05B 3/146* (2013.01); *H05B 3/34* (2013.01); *A24F 40/20* (2020.01); *A61M 2205/0266* (2013.01); *A61M 2205/3368* (2013.01); *F21Y 2115/10* (2016.08); *G06F 3/02* (2013.01); *H05B 2203/021* (2013.01)

(56) References Cited

U.S. PATENT DOCUMENTS

| | | |
|---|---|---|
| 2,104,266 A | 1/1938 | McCormick |
| 2,158,928 A | 5/1939 | Deich |
| 2,159,698 A | 5/1939 | Harris et al. |
| 2,177,636 A | 10/1939 | Coffelt et al. |
| 2,195,260 A | 3/1940 | Rasener |
| 2,830,597 A | 4/1958 | Kummli |
| 2,860,638 A | 11/1958 | Bartolomeo |
| 2,935,987 A | 5/1960 | Ackerbauer |
| 3,200,819 A | 8/1965 | Gilbert |
| 3,292,634 A | 12/1966 | Beucler |
| 3,443,827 A | 5/1969 | Acker et al. |
| 3,456,645 A | 7/1969 | Brock |
| 3,565,071 A | 2/1971 | Sanford Cobb et al. |
| 3,610,880 A | 10/1971 | Kreiberg |
| 3,675,661 A | 7/1972 | Weaver |
| 3,707,017 A | 12/1972 | Paquette |
| 3,792,704 A | 2/1974 | Parker |
| 3,810,258 A | 5/1974 | Mathauser |
| 3,815,597 A | 6/1974 | Goettelman |
| 4,020,853 A | 5/1977 | Nuttall |
| 4,036,224 A | 7/1977 | Choporis et al. |
| 4,049,005 A | 9/1977 | Hernandez et al. |
| 4,066,088 A | 1/1978 | Ensor |
| 4,175,571 A | 11/1979 | Swanson |
| 4,215,708 A | 8/1980 | Bron |
| 4,219,032 A | 8/1980 | Tabatznik et al. |
| 4,269,203 A | 5/1981 | Corbett |
| 4,303,083 A | 12/1981 | Burruss, Jr. |
| 4,506,683 A | 3/1985 | Cantrell et al. |
| 4,534,367 A | 8/1985 | Newsome |
| 4,648,393 A | 3/1987 | Landis et al. |
| 4,708,151 A | 11/1987 | Shelar |
| 4,793,365 A | 12/1988 | Sensabaugh, Jr. et al. |
| 4,819,665 A | 4/1989 | Roberts et al. |
| 4,848,374 A | 7/1989 | Chard et al. |
| 4,944,317 A * | 7/1990 | Thal ............... A24D 1/14 131/348 |
| 4,947,874 A | 8/1990 | Brooks et al. |
| 4,947,875 A | 8/1990 | Brooks et al. |
| 4,967,774 A | 11/1990 | White |
| 4,987,908 A | 1/1991 | Sprinkel et al. |
| 5,020,548 A | 6/1991 | Farrier et al. |
| 5,027,836 A | 7/1991 | Shannon et al. |
| 5,050,621 A | 9/1991 | Creighton et al. |
| 5,060,671 A | 10/1991 | Counts et al. |
| 5,105,838 A | 4/1992 | White et al. |
| 5,144,962 A | 9/1992 | Counts et al. |
| 5,152,456 A | 10/1992 | Ross et al. |
| 5,154,192 A | 10/1992 | Sprinkel et al. |
| 5,183,062 A | 2/1993 | Clearman et al. |
| 5,203,355 A | 4/1993 | Clearman et al. |
| 5,249,586 A | 10/1993 | Morgan et al. |
| 5,261,424 A | 11/1993 | Sprinkel, Jr. |
| 5,269,327 A | 12/1993 | Counts et al. |
| 5,296,685 A | 3/1994 | Burstein et al. |
| 5,303,720 A | 4/1994 | Banerjee et al. |
| 5,456,269 A | 10/1995 | Kollasch |
| 5,479,948 A | 1/1996 | Counts et al. |
| 5,497,791 A | 3/1996 | Bowen et al. |
| 5,505,214 A | 4/1996 | Collins et al. |
| 5,529,078 A | 6/1996 | Rehder et al. |
| 5,551,416 A | 9/1996 | Stimpson et al. |
| 5,564,442 A | 10/1996 | MacDonald et al. |
| 5,573,692 A | 11/1996 | Das et al. |
| 5,649,552 A | 7/1997 | Cho et al. |
| 5,649,554 A | 7/1997 | Sprinkel et al. |
| 5,666,977 A | 9/1997 | Higgins et al. |
| 5,730,118 A | 3/1998 | Hermanson |
| 5,819,756 A | 10/1998 | Mielordt |
| 5,843,014 A | 12/1998 | Lattin et al. |
| 5,894,841 A | 4/1999 | Voges |
| 5,931,828 A | 8/1999 | Durkee |
| 5,954,979 A | 9/1999 | Counts et al. |
| 6,040,560 A | 3/2000 | Fleischhauer et al. |
| 6,089,857 A | 7/2000 | Matsuura et al. |
| 6,095,153 A | 8/2000 | Kessler et al. |
| 6,155,268 A | 12/2000 | Takeuchi |
| 6,164,287 A * | 12/2000 | White ............... A24F 47/008 131/194 |
| 6,196,232 B1 | 3/2001 | Chkadua |
| 6,272,933 B1 | 8/2001 | Gradon et al. |
| 6,324,261 B1 | 11/2001 | Merte |
| 6,407,371 B1 | 6/2002 | Toya et al. |
| 6,513,524 B1 | 2/2003 | Storz |
| 6,532,965 B1 | 3/2003 | Abhulimen et al. |
| 6,603,924 B2 | 8/2003 | Brown et al. |
| 6,612,404 B2 | 9/2003 | Sweet et al. |
| 6,772,756 B2 * | 8/2004 | Shayan ............... A24F 40/48 128/203.26 |
| 6,810,883 B2 | 11/2004 | Felter et al. |
| 6,827,573 B2 | 12/2004 | St. Charles et al. |
| 6,889,687 B1 | 5/2005 | Olsson |
| 7,019,491 B2 | 3/2006 | Bozzone et al. |
| 7,434,584 B2 | 10/2008 | Steinberg |
| 7,530,352 B2 | 5/2009 | Childers et al. |
| 7,801,573 B2 | 9/2010 | Yazdi et al. |
| 7,832,410 B2 | 11/2010 | Hon |
| 8,251,060 B2 | 8/2012 | White et al. |
| 8,371,310 B2 | 2/2013 | Brenneise |
| 8,387,612 B2 | 3/2013 | Damani et al. |
| 8,714,150 B2 | 5/2014 | Alelov |
| 2001/0015209 A1 | 8/2001 | Zielke |
| 2002/0029779 A1 | 3/2002 | Schmidt et al. |
| 2002/0078951 A1 | 6/2002 | Nichols et al. |

(56) References Cited

U.S. PATENT DOCUMENTS

| | | |
|---|---|---|
| 2003/0005926 A1 | 1/2003 | Jones et al. |
| 2003/0033055 A1 | 2/2003 | McRae et al. |
| 2003/0125075 A1 | 7/2003 | Klovborg |
| 2003/0150451 A1 | 8/2003 | Shayan |
| 2004/0031495 A1 | 2/2004 | Steinberg |
| 2004/0089314 A1 | 5/2004 | Felter et al. |
| 2004/0090539 A1 | 5/2004 | Kim et al. |
| 2004/0173229 A1 | 9/2004 | Crooks et al. |
| 2004/0187879 A1 | 9/2004 | Iordan |
| 2004/0221857 A1 | 11/2004 | Dominguez |
| 2004/0237974 A1 | 12/2004 | Min |
| 2005/0016550 A1 | 1/2005 | Katase |
| 2005/0022806 A1 | 2/2005 | Beaumont et al. |
| 2005/0067503 A1 | 3/2005 | Katase |
| 2005/0134215 A1 | 6/2005 | Bozzone et al. |
| 2005/0150488 A1 | 7/2005 | Dave |
| 2005/0251289 A1 | 11/2005 | Bonney et al. |
| 2005/0268911 A1 | 12/2005 | Cross et al. |
| 2006/0102175 A1 | 5/2006 | Nelson |
| 2007/0006889 A1 | 1/2007 | Kobal et al. |
| 2007/0045288 A1 | 3/2007 | Nelson |
| 2007/0062523 A1 | 3/2007 | Sexton et al. |
| 2007/0125372 A1 | 6/2007 | Chen |
| 2007/0125765 A1 | 6/2007 | Nelson |
| 2007/0267031 A1 | 11/2007 | Hon |
| 2007/0283972 A1 | 12/2007 | Monsees et al. |
| 2008/0000763 A1 | 1/2008 | Cove |
| 2008/0023003 A1 | 1/2008 | Rosenthal |
| 2008/0065176 A1 | 3/2008 | Zhang et al. |
| 2008/0092912 A1 | 4/2008 | Robinson et al. |
| 2008/0121244 A1 | 5/2008 | Bryman et al. |
| 2008/0150482 A1 | 6/2008 | Yazdi et al. |
| 2008/0214103 A1 | 9/2008 | Nelson et al. |
| 2008/0216828 A1 | 9/2008 | Wensley et al. |
| 2008/0233053 A1 | 9/2008 | Gross et al. |
| 2008/0257367 A1 | 10/2008 | Paterno et al. |
| 2009/0056708 A1 | 3/2009 | Stenzler et al. |
| 2009/0071469 A1 | 3/2009 | Abrams |
| 2009/0095287 A1 | 4/2009 | Emarlou |
| 2009/0110379 A1 | 4/2009 | Mcghin et al. |
| 2009/0111287 A1 | 4/2009 | Lindberg et al. |
| 2009/0126745 A1 | 5/2009 | Hon |
| 2009/0133691 A1 | 5/2009 | Yamada et al. |
| 2009/0141196 A1 | 6/2009 | Basner et al. |
| 2009/0151717 A1 | 6/2009 | Bowen et al. |
| 2009/0177253 A1 | 7/2009 | Darm et al. |
| 2009/0178672 A1 | 7/2009 | Mullinger et al. |
| 2009/0192443 A1 | 7/2009 | Collins, Jr. |
| 2009/0230117 A1 | 9/2009 | Fernando et al. |
| 2009/0239581 A1 | 9/2009 | Lee |
| 2009/0272379 A1 | 11/2009 | Thorens et al. |
| 2009/0283103 A1 | 11/2009 | Nielsen et al. |
| 2009/0288668 A1 | 11/2009 | Inagaki |
| 2009/0293892 A1 | 12/2009 | Williams et al. |
| 2009/0302019 A1 | 12/2009 | Selenski et al. |
| 2009/0308387 A1 | 12/2009 | Andersen et al. |
| 2010/0006092 A1 | 1/2010 | Hale et al. |
| 2010/0156193 A1 | 6/2010 | Rhodes et al. |
| 2010/0163063 A1 | 7/2010 | Fernando et al. |
| 2010/0242956 A1 | 9/2010 | Yamada et al. |
| 2010/0242974 A1 | 9/2010 | Pan |
| 2010/0313901 A1 | 12/2010 | Fernando et al. |
| 2011/0030706 A1 | 2/2011 | Gibson et al. |
| 2011/0036346 A1 | 2/2011 | Cohen et al. |
| 2011/0040235 A1 | 2/2011 | Castel |
| 2011/0041861 A1 | 2/2011 | Sebastian et al. |
| 2011/0094523 A1 | 4/2011 | Thorens et al. |
| 2011/0097660 A1 | 4/2011 | Buzzetti |
| 2011/0105096 A1 | 5/2011 | Dods et al. |
| 2011/0108023 A1 | 5/2011 | McKinney et al. |
| 2011/0120482 A1 | 5/2011 | Brenneise |
| 2011/0126831 A1 | 6/2011 | Fernandez Pernia |
| 2011/0132992 A1 | 6/2011 | Christopher et al. |
| 2011/0226236 A1 | 9/2011 | Buchberger |
| 2011/0226266 A1 | 9/2011 | Tao |
| 2011/0236002 A1 | 9/2011 | Oglesby et al. |
| 2011/0240047 A1 | 10/2011 | Adamic |
| 2011/0253139 A1 | 10/2011 | Guthrie et al. |
| 2011/0265788 A1 | 11/2011 | Wu |
| 2012/0086391 A1 | 4/2012 | Smith |
| 2012/0097660 A1 | 4/2012 | Bao |
| 2012/0199572 A1 | 8/2012 | Shen et al. |
| 2012/0255546 A1 | 10/2012 | Goetz et al. |
| 2012/0325227 A1 | 12/2012 | Robinson et al. |
| 2013/0042864 A1 | 2/2013 | Adler et al. |
| 2013/0042865 A1 | 2/2013 | Monsees et al. |
| 2013/0099025 A1 | 4/2013 | McDonnell |
| 2013/0099757 A1 | 4/2013 | Ham |
| 2013/0255702 A1 | 10/2013 | Griffith, Jr. et al. |
| 2013/0298905 A1 | 11/2013 | Levin et al. |
| 2013/0312742 A1 | 11/2013 | Monsees et al. |
| 2015/0101606 A1 | 4/2015 | White |
| 2015/0305409 A1 | 10/2015 | Verleur et al. |
| 2016/0007654 A1 | 1/2016 | Zhu |
| 2016/0331034 A1 | 11/2016 | Cameron |

FOREIGN PATENT DOCUMENTS

| | | |
|---|---|---|
| CH | 508360 A | 6/1971 |
| CN | 86204805 U | 6/1987 |
| CN | 87101954 A | 10/1987 |
| CN | 86102917 A | 11/1987 |
| CN | 87202001 U | 12/1987 |
| CN | 88100383 A | 3/1988 |
| CN | 1043077 A | 6/1990 |
| CN | 1044391 A | 8/1990 |
| CN | 2103908 U | 5/1992 |
| CN | 2121128 U | 11/1992 |
| CN | 1087497 A | 6/1994 |
| CN | 1191696 A | 9/1998 |
| CN | 1195270 A | 10/1998 |
| CN | 2293957 Y | 10/1998 |
| CN | 1216903 A | 5/1999 |
| CN | 1233158 A | 10/1999 |
| CN | 1260688 A | 7/2000 |
| CN | 1284464 A | 2/2001 |
| CN | 1333657 A | 1/2002 |
| CN | 1397237 A | 2/2003 |
| CN | 1541577 A | 11/2004 |
| CN | 1575135 A | 2/2005 |
| CN | 1575136 A | 2/2005 |
| CN | 1575673 A | 2/2005 |
| CN | 1630476 A | 6/2005 |
| CN | 1633247 A | 6/2005 |
| CN | 100566769 C | 12/2009 |
| CN | 100593982 C | 3/2010 |
| CN | 201630238 U | 11/2010 |
| CN | 101932352 A | 12/2010 |
| CN | 101557728 B | 4/2011 |
| CN | 103929985 A | 7/2014 |
| DE | 4200639 A1 | 7/1992 |
| DE | 19854005 A1 | 5/2000 |
| DE | 19854009 A1 | 5/2000 |
| DE | 19854012 A1 | 5/2000 |
| EP | 0129985 A1 | 1/1985 |
| EP | 0241698 A1 | 10/1987 |
| EP | 0295122 A2 | 12/1988 |
| EP | 0311581 A1 | 4/1989 |
| EP | 0336457 A2 | 10/1989 |
| EP | 354661 A2 | 2/1990 |
| EP | 0409566 A1 | 1/1991 |
| EP | 0430559 A2 | 6/1991 |
| EP | 0858744 A1 | 8/1998 |
| EP | 0893071 A1 | 1/1999 |
| EP | 0845220 B1 | 9/2003 |
| FR | 409989 A | 5/1910 |
| FR | 2654002 A1 | 5/1991 |
| GB | 873410 A | 7/1961 |
| GB | 1025630 A | 4/1966 |
| GB | 1185887 A | 3/1970 |
| GB | 1213318 A | 11/1970 |
| GB | 2115676 A | 9/1983 |
| JP | S59-178456 A | 10/1984 |
| JP | S61-092295 U | 6/1986 |

(56) References Cited

FOREIGN PATENT DOCUMENTS

| | | |
|---|---|---|
| JP | 62-224277 | 10/1987 |
| JP | S62-278975 A | 12/1987 |
| JP | H02-124082 A | 5/1990 |
| JP | H03-049671 A | 3/1991 |
| JP | H05-115272 A | 5/1993 |
| JP | 08-000942 | 6/1996 |
| JP | 2006/3239440 | 11/1996 |
| JP | H11-178563 A | 7/1999 |
| JP | 2000236865 A | 9/2000 |
| JP | 2005034021 A | 2/2005 |
| JP | 2005-058421 A | 3/2005 |
| JP | 2005506080 A | 3/2005 |
| JP | 2009148233 A | 7/2009 |
| JP | 2010/088653 A | 4/2010 |
| JP | 2011/066476 A | 3/2011 |
| KR | 10-0178387 | 11/1998 |
| KR | 1019920017583 | 2/1999 |
| KR | 10-1999-0037661 A | 5/1999 |
| KR | 20-1999-0015691 A | 5/1999 |
| KR | 100193885 B1 | 6/1999 |
| KR | 20070112908 A | 11/2007 |
| KR | 2009/0010954 A | 1/2009 |
| KR | 2009/0023742 A | 3/2009 |
| KR | 20110053506 A | 5/2011 |
| KR | 10-20140090138 A | 7/2014 |
| NL | 7809640 A | 3/1979 |
| TW | 200836649 A | 9/2008 |
| TW | M413347 U | 10/2011 |
| UA | 88052 C2 | 9/2009 |
| WO | WO-9406314 A1 | 3/1994 |
| WO | WO-9418860 A1 | 9/1994 |
| WO | WO-9501137 A1 | 1/1995 |
| WO | WO-9741744 A1 | 11/1997 |
| WO | WO-97/048293 A1 | 12/1997 |
| WO | WO-9748295 A1 | 12/1997 |
| WO | WO-9963844 A1 | 12/1999 |
| WO | WO-0028843 A1 | 5/2000 |
| WO | WO-0170054 A1 | 9/2001 |
| WO | WO-03/025527 A2 | 3/2003 |
| WO | WO-03068300 A1 | 8/2003 |
| WO | WO-03082031 A1 | 10/2003 |
| WO | WO-2004041007 A2 | 5/2004 |
| WO | WO-2004064548 A1 | 8/2004 |
| WO | WO-2004089126 A1 | 10/2004 |
| WO | WO-2005/025654 A1 | 3/2005 |
| WO | WO-2005046363 A2 | 5/2005 |
| WO | WO-2006082571 A1 | 8/2006 |
| WO | WO-2007/012007 A2 | 1/2007 |
| WO | WO-2007010411 A2 | 1/2007 |
| WO | WO-2008/015918 A1 | 2/2008 |
| WO | WO-2009118085 A1 | 10/2009 |
| WO | WO-2010140841 A2 | 12/2010 |

OTHER PUBLICATIONS

U.S. Appl. No. 12/482,376, filed Jun. 10, 2009, U.S. Pat. No. 8,915,254.
U.S. Appl. No. 12/482,379, filed Jun. 10, 2009, U.S. Pat. No. 8,925,555.
U.S. Appl. No. 13/587,416, filed Aug. 16, 2012, U.S. Pat. No. 9,408,416.
U.S. Appl. No. 13/837,438, filed Mar. 15, 2013, US 2013-0312742.
U.S. Appl. No. 14/578,193, filed Dec. 19, 2014, U.S. Pat. No. 10,834,964.
U.S. Appl. No. 15/165,954, filed May 26, 2016, U.S. Pat. No. 10,244,793.
U.S. Appl. No. 15/165,972, filed May 26, 2016, US 2016-0345631.
U.S. Appl. No. 15/166,001, filed May 26, 2016, US 2016-0262459.
U.S. Appl. No. 15/261,823, filed Sep. 9, 2016, US 2016-0374400.
U.S. Appl. No. 15/368,539, filed Dec. 2, 2016, US 2017-0079331.
U.S. Appl. No. 16/248,852, filed Jan. 16, 2019, US 2020-0221759.
U.S. Appl. No. 16/372,354, filed Apr. 1, 2019, US 2019-0223510.
U.S. Appl. No. 16/434,295, filed Jun. 7, 2019.

\* cited by examiner

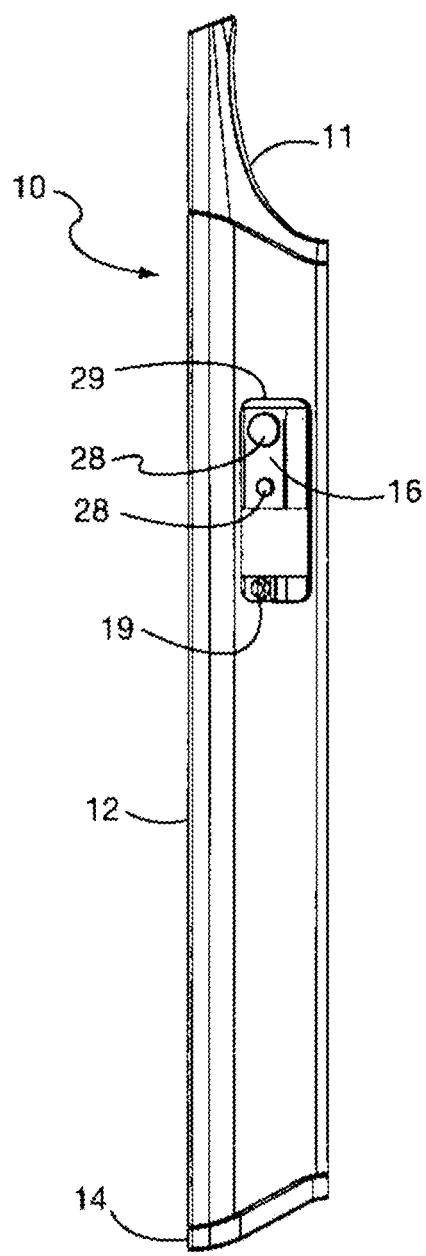
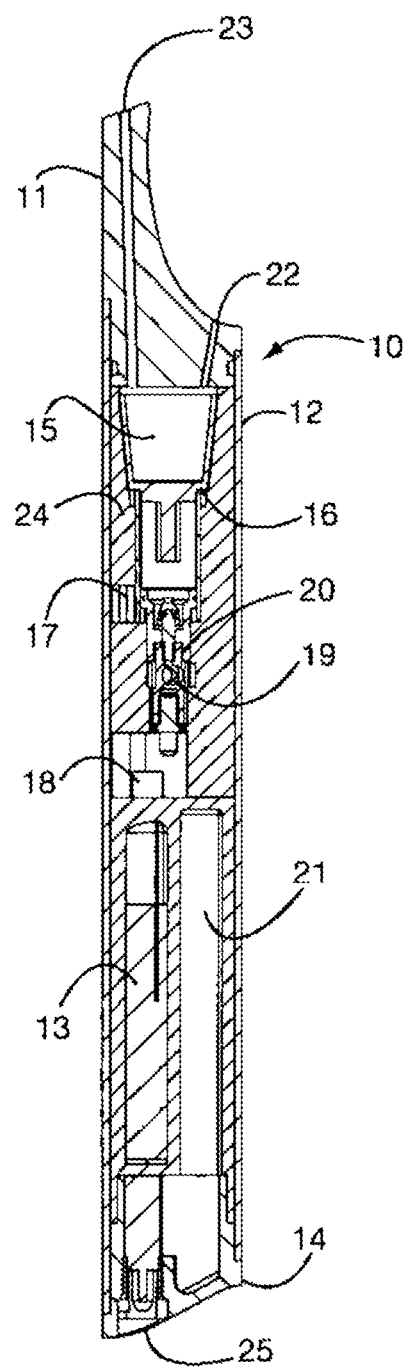
FIG. 1
FIG. 2

DEVICES FOR VAPORIZATION OF A SUBSTANCE

CROSS REFERENCE TO RELATED APPLICATIONS

This application is a continuation of U.S. patent application Ser. No. 15/165,954, filed May 26, 2016. U.S. patent application Ser. No. 15/165,954 is a continuation-in-part of U.S. patent application Ser. No. 14/578,193, filed Dec. 19, 2014, which is a continuation of U.S. patent application Ser. No. 11/485,168, filed Jul. 11, 2006, which claims the benefit of U.S. Provisional Application No. 60/700,105, filed Jul. 19, 2005, each of which is incorporated herein by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are smoking devices, particularly to smoking articles which produce vapor by heat transfer to the cartridge by conduction, convection, and/or radiation for smoke and flavor. The devices and systems described herein include self-contained vaporization devices, and more particularly, low-temperature vaporization devices for use with a vaporizable material such as tobacco and tobacco products. These devices may include an elongated main body with a mouthpiece at one end and an attached tubular casing having a vaporization chamber and a heater. The mouthpiece and the casing may form a unitary unit.

BACKGROUND

Smoking devices, such as cigarette holders and pipes are well known in the art for providing flavored vapor from a smokeable substance to a user for therapeutic and smoking pleasure. However, existing devices used have no control of heating and combustion of the tobacco products. The devices tend to produce toxic, tarry and carcinogenic byproducts which are harmful and also impart a bitter and burnt taste to a mouth of a user.

In an effort to overcome these deficiencies, there have been numerous attempts to provide a device structure and the substance for producing vapor for smoking which is free from harmful by-product and would provide a cool and soothing vapor for smoking.

For example, U.S. Patent Application Publication No. 2004/0237974 A1, published on Dec. 2, 2004 for Min discloses a filtering cigarette and cigar holder which removes tar and nicotine from the tobacco smoke.

U.S. Patent Application Publication No. 2004/0031495 A1, published on Feb. 19, 2004 for Steinberg discloses a vaporization pipe with flame filter which uses a flame to vaporize the smoking sub stance.

U.S. Pat. No. 6,164,287, issued Dec. 26, 2000 to White, describes a smoking device which produces smoke from tobacco at low temperatures, without producing harmful byproducts.

U.S. Pat. No. 4,848,374, issued Jul. 18, 1989 to Chard et al describe a smoking device to vaporize aerosol precursor, an event which precedes condensation to mainstream aerosol precursor by contact with heated surface rather than by hot gases into the mouth of a smoker.

U.S. Pat. No. 4,219,032, issued Aug. 26, 1980 to Tabatznik et al describe a smoking device wherein an extracted smoke is cooled by passing it through a suitable liquid to provide a soothing smoke.

U.S. Pat. No. 4,020,853, issued May 3, 1977 to Nuttall, describes a smoking pipe made of ceramic material such as colored and ornamental porcelain for enhancing the artistic look, and also to provide a circulating air to keep the outer wall of the pipe cool and safe for handling.

U.S. Pat. No. 3,792,704, issued Feb. 19, 1974 to Parker, describes a pipe tobacco smoking system, wherein the pipe and the tobacco capsule are mutually designed to yield a slim-line smoking combination that can be manufactured from relatively low temperature thermo-plastic material.

SUMMARY OF THE DISCLOSURE

Some variations of the devices and systems described herein are drawn to novel vaporizing device consisting of a mouthpiece and a casing having a heater, a low temperature vaporization chamber, a fuel tank, an igniter with control means for maintaining equilibrium point by keeping the operating temperature below 400° F., preferably below 350° F., during vaporization, whereby a thermal regulator may be used to control flow rate of the fuel to maintain a stable operating temperature.

These devices may provide a mouthpiece made of a high temperature food-safe material, such as ceramic, glass, or high temperature plastics known as PEI resin (brand name Ultem). However, suitable plastic or wood, etc., could also be used but would additionally require an insulating material that would prevent excessive heat reaching the user's lips.

Additionally, air inlets are directed downwards, so that fresh ambient air drawn through mixes with the vapor generated into the vaporization chamber located above the smokeable substance cartridge, which is extracted from the cartridge by inlets located below the cartridge and drawn into user's mouth for inhalation.

These devices and systems may also provide air inlet or inlets having a diameter and direction sized to admit ambient air into the chamber to heat up the substance and not affect the operating temperature and also regulating the velocity of ambient air entering and mixing with the vapor generated from combustion, radiation and convection in the chamber at such a rate that the proportionate inhalation passage provides a perception to the user as if the smoke is drawn through a cigarette.

These devices and systems may also provide a heater which is separated from the vapor chamber by an insulating medium such as ring made of PTFE, ceramic or other insulating material and thereby preventing the exhaust gases produced by the heater from entering and contaminating the vapor in the vaporization chamber collected for inhalation.

These devices and systems may also provide a heater is formed of a conductive shell and a catalyst, the shell may be of one or more material formed by welding or pressing together. Whereas, the catalyst could be of platinum or palladium impregnated metal or glass or other suitable material, which provides for efficient flameless combustion of the fuel and glows red when heated to indicate that the device is activated. Additionally, a feedback loop could be employed to regulate the desired temperature.

In variations including a cartridge (e.g., of tobacco), the tobacco cartridge may be formed and shaped for easier insertion into the heating chamber and to snugly fit into the cavity of the heating chamber for improved thermal conduction and vaporization. The cartridges may be formed and wrapped into wrapper which does not produce significant amount of harmful gases.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 is a side view of a portable vaporization device, according to one embodiment of the present invention.

FIG. 2 is a sectional view of the same embodiment.

DETAILED DESCRIPTION

Figure 3:
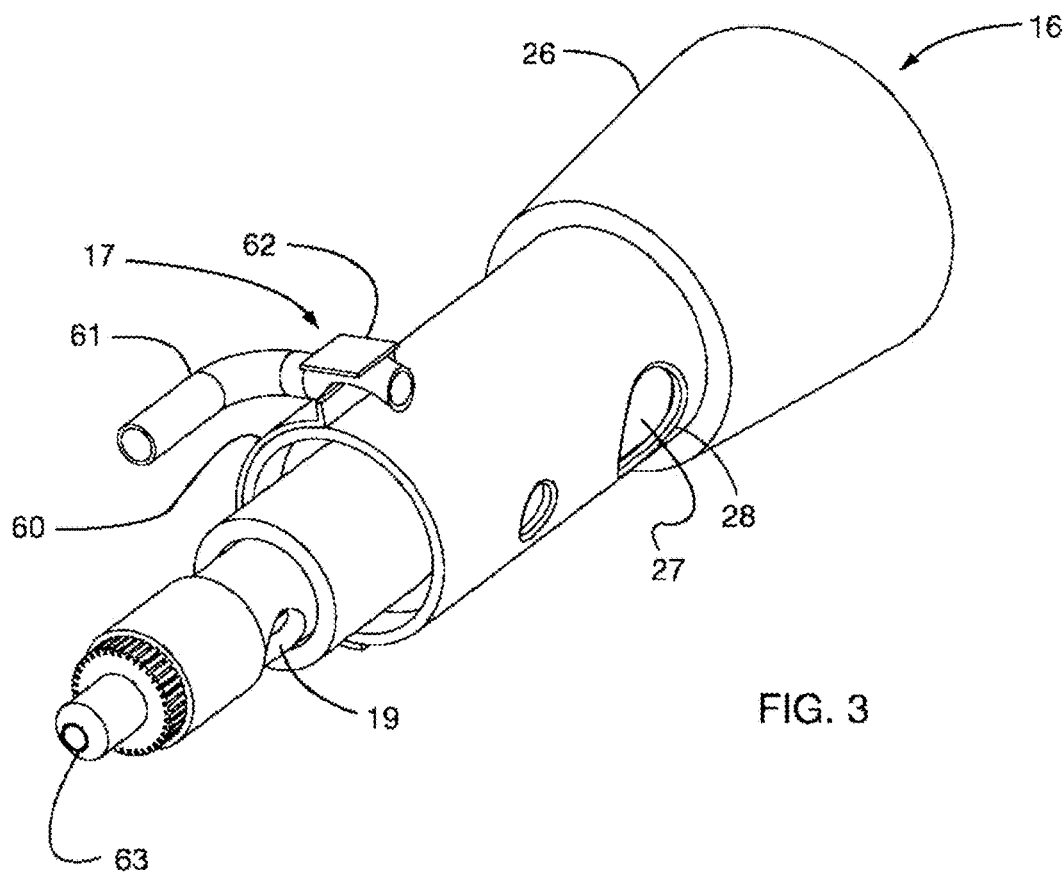
FIG. 3 is a perspective view of a heater, according to the same embodiment.

Referring to FIG. 1 and FIG. 2, the exterior of the device 10 comprises a mouthpiece 11, a tubular case 12, and the base 14 of a butane tank 21. The mouthpiece is removable and creates an airtight seal with the interior of the case. With the mouthpiece removed, a tobacco cartridge (FIG. 5) is introduced to vaporization chamber 15 of a heater 16. The mouthpiece is then reinserted to close the device. Thus, as shown in FIGS. 1 and 2, removal of the mouthpiece exposes the vaporization chamber and replacement of the mouthpiece closes the vaporization chamber.

The mouthpiece is made of a high-temperature and food-safe material such as ceramic, glass, or various high-temperature plastics such as PEI resin (brand name Ultem). Design is simplified by use of high temperature materials, but standard plastics or wood, etc., could also be used with the addition of an insulating component that prevents any excessive heat from reaching the user's lips.

To activate the device, the butane tank is pulled axially outward, partially removing it from the case. This starts the flow of butane by opening a master valve 18, and then activating a piezoelectric igniter 13. The tank remains in the partially removed position for the duration of use. While the master valve is open, butane flows through a thermal regulator 17, and into the carburetor 20. Ambient air enters the case through slot 19. A venturi in the carburetor entrains air, causing it to mix with the butane. The mixture then flows into the heater 16.

The lead of the ignitor is positioned in the heater. With the spark of the ignitor (immediately following the start of gas flow) the gas ignites and heat starts conducting throughout the heater. Heat transfers to the cartridge by conduction, convection, and radiation. The cartridge is shaped to fill the chamber, so as to maximize surface contact for thermal conduction.

As the cartridge heats, vapor generates within the cartridge and in the space immediately above it. When a user draws on the device, fresh air enters through air inlet 22, mixes with the vapor, and the mixture is delivered to the user via the inhalation passage 23. In one embodiment, the air inlet or inlets are directed downward, so as to improve the extraction of vapor from the cartridge. They could also be directed along a diagonal through the mouthpiece, or laterally through the case itself, above the cartridge.

FIG. 3 depicts a detailed view of the heater 16. The heater comprises a thermally conductive shell 26 and catalyst 27. The shell could be comprised of one material, or a combination of materials welded or pressed together. The catalyst could be platinum- or palladium-impregnated metal or glass, or other suitable material known to those skilled in the art. The catalyst provides for efficient flame-less combustion of the butane. The vent 28 of the heater is positioned such that it is visible through the slot 29 of the body as shown in FIG. 1. This allows the user to see the catalyst which, when heated, can glow red to indicate that the device has been activated. Thus, the window (slot 29) shown in FIG. 1 extends through the elongated main body (tubular case 12). Thus, FIG. 3 is one example of a portable device for generating an inhalable vapor from a botanical material including an elongate body and a vaporization chamber 15 within the body that is configured to hold a vaporizable material therein. As just described, the window 29 through the body in this example is configured to allow a user to see a glow of the heater through the window to indicate that the heater has been activated.

Referring again to FIG. 3, adjacent to the heater and in intimate thermal contact is the thermal regulator 17. As the temperature of the heater increases, so does that of the regulator. The regulator is designed to restrict the flow of butane as the temperature increases, thus creating a feedback loop. In one embodiment, the regulator consists of a bimetallic strip 60 and silicone tubing 61 which is the conduit of the butane. The two are arranged such that as the bimetallic strip heats up, it curls to pinch the silicone tube and thereby restrict the flow of butane. The reduced flow of butane results in less heat generated. The heater subsequently cools down, and so does the regulator, allowing more butane to flow again. The overall result is that a stable operating temperature is established in the heater. Such a system can be readily tuned to achieve an operating temperature that varies by less than +/−5 degrees Fahrenheit.

The regulator further comprises a moveable backplate 62 which allows adjustability of the operating temperature by adjusting the temperature at which the bi-metallic actuator closes the tube valve. This is to be performed once at manufacture, to calibrate the device. In alternate embodiments, a control means could be used to allow the target temperature of the device changed during operation.

In one embodiment, the regulator comprises in part a bi-metallic strip and silicone tubing valve. In alternate embodiments, the regulator could be comprised of other materials and configurations, as described later.

For the purposes of vaporizing most botanicals in this device, the desired operating temperature is below 400° F.; preferably below 350° F.

In one embodiment, the air inlet diameter is sized such that inhalation is somewhat inhibited. This allows time for ambient air entering the chamber to heat up and not affect operating temperature considerably. It also increases velocity of the entering air, which improves circulation and mixing in the vaporization chamber. It also creates a partial vacuum, lowering the vapor point temperature for material contained in the vaporization chamber. The reduction in draw rate can also serve to give the impression of drawing on a cigarette or pipe. Both the fresh air inlet and inhalation passage can be adjusted to provide appropriate draw rate for the operating temperature of the device, and the perception intended for the user.

Once the cartridge is consumed, the device is turned off by pushing the tank back into the case, closing the master valve. The spent tobacco cartridge is removed by opening the device and turning the body over. In one embodiment, the cartridge simply falls out. In alternate embodiments, a mechanism could be used to quickly and easily remove the cartridge. This mechanism could include, but does not require, the use of a pin or slide part to eject the cartridge as another part of the device is moved or removed. The removal mechanism could also involve introduction of a foreign object.

In an alternate embodiment, the mouthpiece is permanently attached to the body. In that case, the vaporization chamber could be accessed by operating a sliding or hinged door, or similar means, built into the device.

The heater of the device is fitted into the case with an insulator 24. The insulator could be made of PEI (brand name Ultem), ceramic, or other insulating material. The insulator serves to minimize thermal transfer from the heater to the case, while creating an air-tight seal. The seal prevents exhaust gases produced by the heater from entering the vaporization chamber. Exhaust gases are instead vented out the case slots. Since the air inlet is distant from the slots, there is substantially no contamination of the inhaled vapor mixture by heater exhaust gases.

In an alternate embodiment, the insulator could be a partially hollow shell, containing a sealed vacuum. In another embodiment, the heater might be sealed directly to the case by braising in a vacuum furnace, so as to create a vacuum between the two and obviate need for an insulator component.

In one embodiment, the tank is made of a translucent material. This allows the user to determine the level of fuel remaining by looking at the base of the tank.

In one embodiment, the case is made of a material that is either a good thermal conductor (such as aluminum), or a poor one (such as ceramics). In both cases, the effect is that the body remains cool enough to touch over a large portion of its surface.

In one embodiment, a bimetallic actuator is used in the regulator. In alternate embodiments, a shape memory alloy actuator such nickel-titanium alloys ("Nitinol") could be used. Alternatively, a paraffin-filled component that expands and contracts to modulate butane flow could be employed. Alternatively, a system could be employed to measure the current temperature, e.g., with a thermocouple sensor and compare it to a prescribed temperature, e.g., with a micro-controller, and by controlling an electromechanical valve, e.g., servo or solenoid valve. In an embodiment with user-selected temperature, as described above, the selected temperature could be used as an input to this system.

In one embodiment, a thermal regulator is used. In an alternate embodiment, the device is constructed without an active regulating element. This could result in reduced complexity and in lowering the overall cost of the device. In this case, the flow of butane is set at a low level. In use, the temperature inside the chamber increases until an equilibrium point where additional heat introduced equals the heat lost to the environment. Heat is lost by conduction through the body of the device, and with the vapor delivered to the user. This equilibrium point determines the operating temperature of the device. By changing the butane flow rate, size and material of the burner, and other factors, the system can be calibrated to provide a fairly stable desired operating temperature.

The principal advantage of the preferred bimetallic regulator feedback loop methods over the equilibrium method is that the operating temperature is not dependent on environmental factors such as ambient temperature and wind.

In one embodiment, a piezo-electric ignitor is used. Other ignitors could be used, such as, a flint starter or battery-powered resistive coil.

In one embodiment, the butane tank is meant to be refillable, and has a port 25 for that purpose. As an alternate embodiment, the tank might be disposable once its fuel is exhausted. A release mechanism such as a pin or cam would be employed allowing the user to quickly remove the depleted tank and replace it with a full one. The replaceable tank might include additional parts of the device including, but not limited to, the ignitor and heater. Butane is one fuel source, but could be replaced by other liquid fuels, such as ethanol.

In alternate embodiments of the present invention, various means of feedback could be used to indicate the following states or metrics of the device: 1) the device is on, 2) the current temperature of the vaporization chamber, 3) the chamber is below a prescribed operating temperature, 4) the chamber has reached a prescribed operating temperature and vapor is ready for consumption (e.g., the device is ready to use), and 5) the chamber has exceeded a prescribed operating temperature. Thus the feedback, such as one or more LEDs on the device may indicate that the device is heating and/or is ready to use.

The means of the feedback includes both physical and electronic implementations. Possibilities include thermochromatic paint, light-emitting diodes and liquid crystal display. The sensing and control means for electronic feedback could be implemented by use of thermocouple and micro-controller, as is known to those skilled in the art.

Active elements contained in botanicals vaporize at different temperatures. In one embodiment, the device is calibrated to establish a single stable temperature, intended for vaporizing solely tobacco or solely chamomile, for example. In alternate embodiments, a control means would be used to select a variety of temperature settings. The user would choose which setting based on the type of cartridge used. The control means could effect a desired temperature mechanically, such as by changing flow rate of the valve, or electronically, such as by electromechanical valve and micro-controller intermediary.

Butane was found to be the most energy-dense and practical fuel source. In alternate embodiments of the invention, the butane heating system is replaced by a battery-powered electric heater or other compact heat source.

Figure 4:
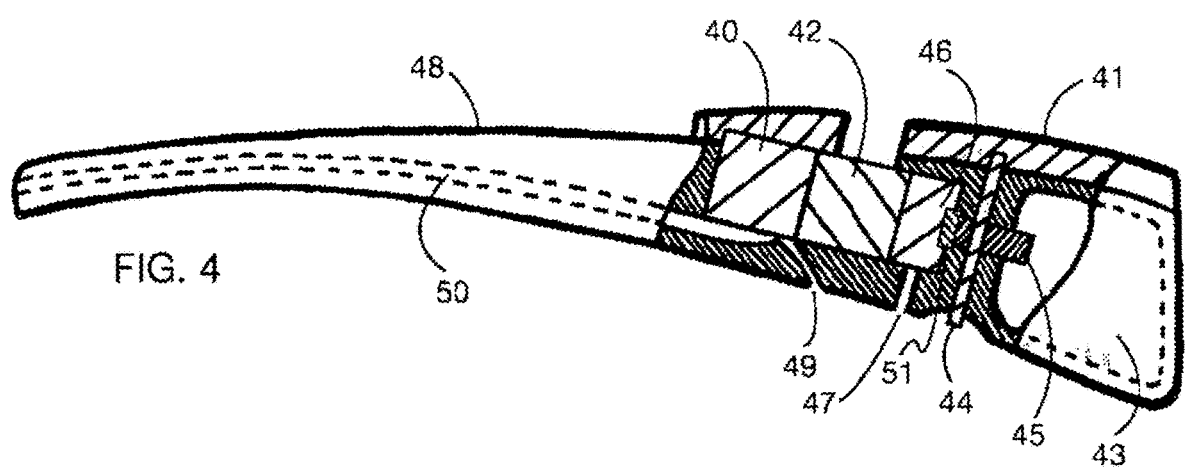
FIG. 4 is a cutaway view of an alternate embodiment according to the present invention.

FIG. 4 depicts a cutaway view of an alternate embodiment which more closely resembles a traditional pipe form. In this embodiment the device retains all of the critical elements from one embodiment. The user inserts a tobacco cartridge 40, under a sliding top piece 41, where the cartridge mates with the heater 42. Fuel held in the tank 43 is released by turning dial 44 to open master valve 45. The fuel travels through the regulator 51, and then through the carburetor 46 where it draws in air through the intake port 47 and catalyzes in a manner similar to that of one embodiment. As the cartridge 40 reaches its operating temperature the user places the mouthpiece 48 in their mouth and draws air in through the inhalation intake port 49 and through the vapor passage 50 where it is pre-cooled.

Figure 5:
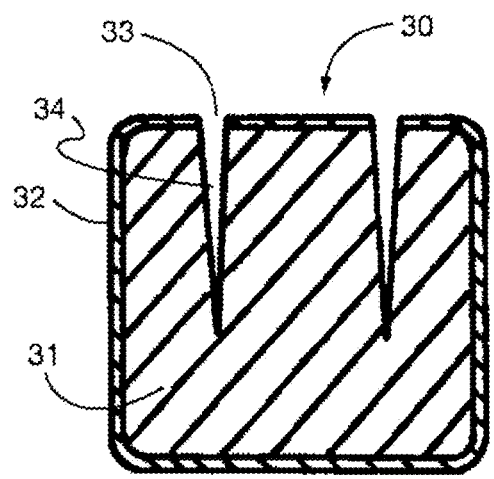
FIG. 5 is a sectional detail view of a tobacco cartridge, according to one embodiment.

FIG. 5 depicts a sectional view of the tobacco cartridge 30. In one embodiment, it consists of tobacco material 31, enclosed in a wrapper 32, with perforations 33, and aeration wells 34. The wrapped cartridge allows for the easy insertion and disposal of tobacco material without creating a mess, while the perforations allow the formed vapor to be released. When the cartridge is used up it can be easily disposed of in its entirety.

Here, tobacco or tobacco material is defined as any combination of natural and synthetic material that can be vaporized for pleasure or medicinal use. As an example, one test cartridge was prepared as embodiment of the present invention using flue-cured tobacco, glycerin, and flavorings. Those skilled in the art of tobacco product manufacture are familiar with these and other ingredients used for cigarettes, cigars, and the like. The test cartridge was produced by chopping tobacco into fine pieces (less than 3 mm diameter, preferably less than 2 mm), adding the other ingredients, and mixing until even consistency was achieved.

In one embodiment, the cartridge is primarily cylindrical. In other embodiments, the form could be modified for various reasons. As an example, the walls of the cartridge might be drafted for easier insertion into the vaporization chamber. Or, the bottom of the cartridge might possess receptacles, which when combined with complimentary features on the surface cavity of the vaporization chamber would allow for more surface contact and hence improved thermal conduction.

Figure 6:
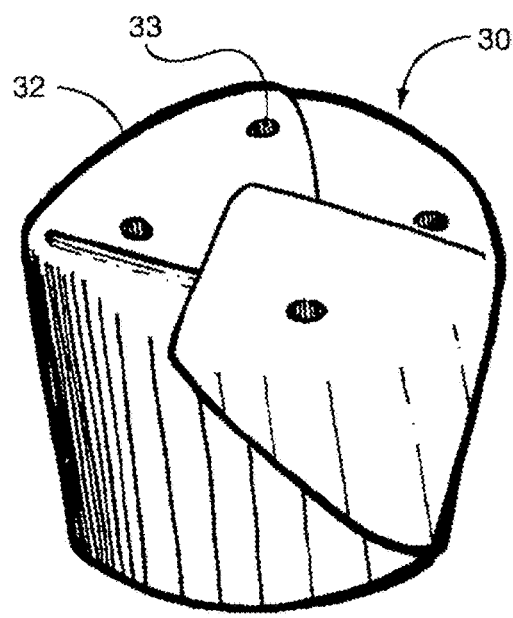
FIG. 6 is a perspective view of a tobacco cartridge, according to one embodiment.

Any material could be used for the wrapper, provided that when heated to the operating temperature, it does not produce significant amounts of harmful gases. Aluminum foil and parchment paper are two examples. With papers, the cartridge would be manufactured in a folded-cup design, similar to that shown in FIG. 6. With films or metal foils, the wrapper could be pressed or blow-molded to the appropriate shape.

During manufacture of one embodiment, the cartridge is enclosed on all sides, and perforated on the top so that vapors can emanate upwards. In the perforation step, or in an additional step, the optional aeration wells would be created.

Figure 7:
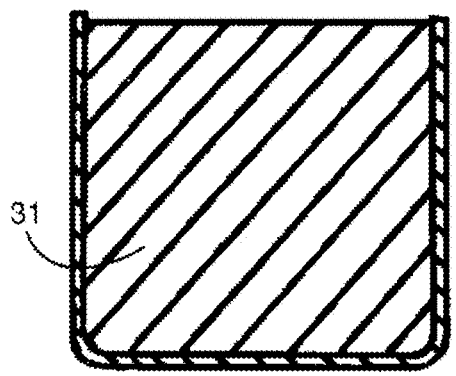
FIG. 7 is a sectional detail view of a tobacco cartridge, according to an alternate embodiment.

In an alternate embodiment, the cartridge might be wrapped on all sides but leaving the top exposed, as shown in FIG. 7. This is possible since the purpose of the wrapper is primarily to prevent tobacco material from touching the sides and bottom of the vaporization chamber.

In another embodiment, the material for the top of the cartridge might be vapor-permeable, such that perforations are not necessary.

In another embodiment, the cartridge as purchased by the user has no openings, but is punctured prior to insertion into the device, or upon introduction to the vaporization device. The latter could be achieved by adding a hollow puncturing means to the mouthpiece part of the device. For example, the inhalation passage of the mouthpiece could be extended by a hollow tube. When the mouthpiece is reinserted to close the device, it pierces the cartridge previously introduced, and allows a path for vapor to exit to the user.

Figure 8:
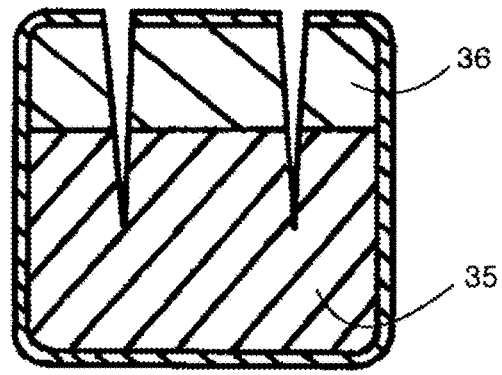
FIG. 8 is a sectional detail view of a tobacco cartridge, according to an alternate embodiment.
Figure 10:
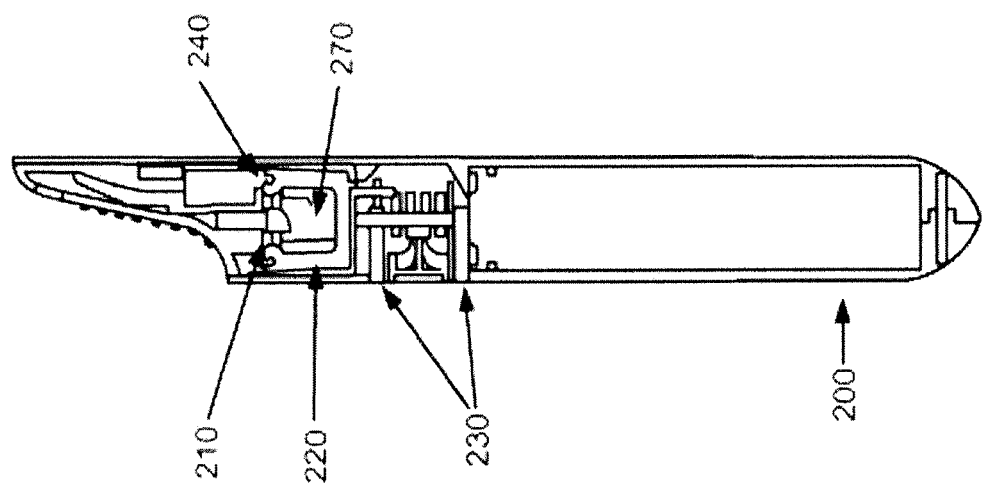
Figure 9:
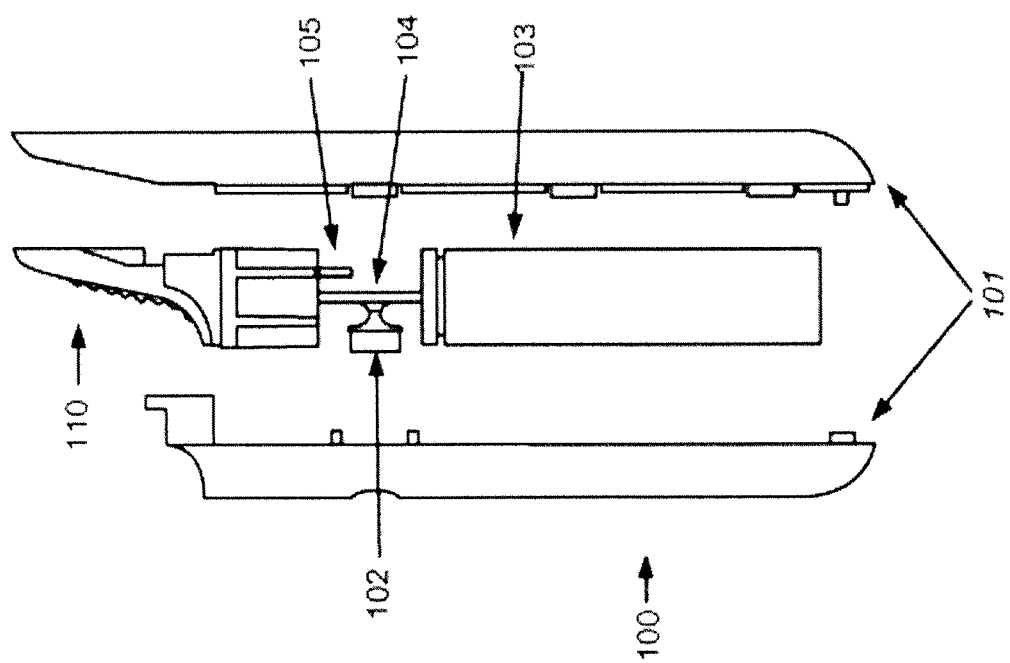
Figure 11B:
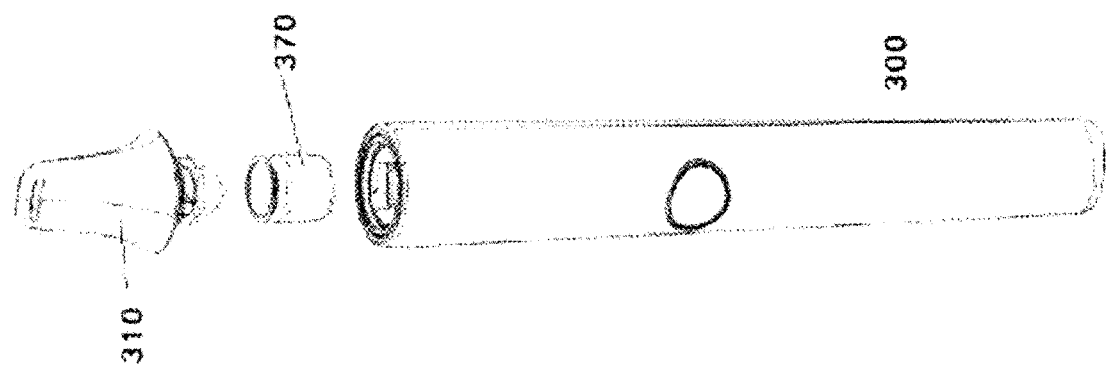
Figure 11A:
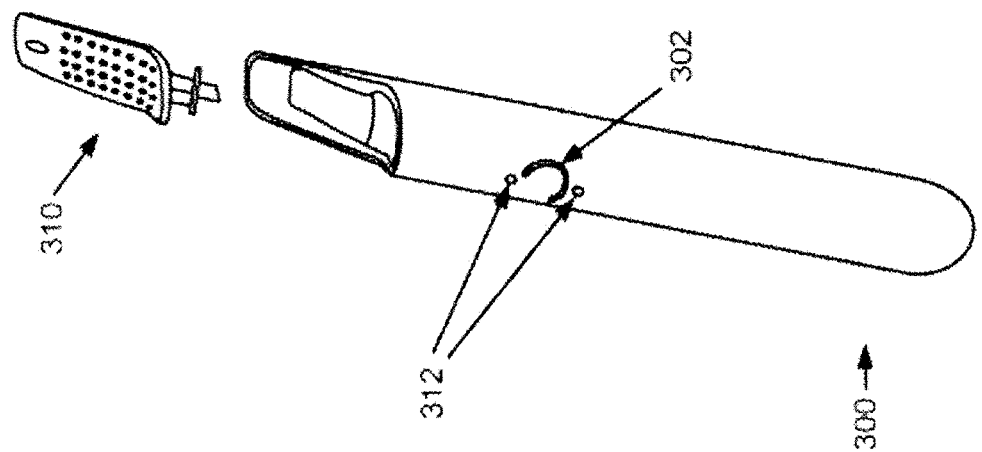
Figure 13:
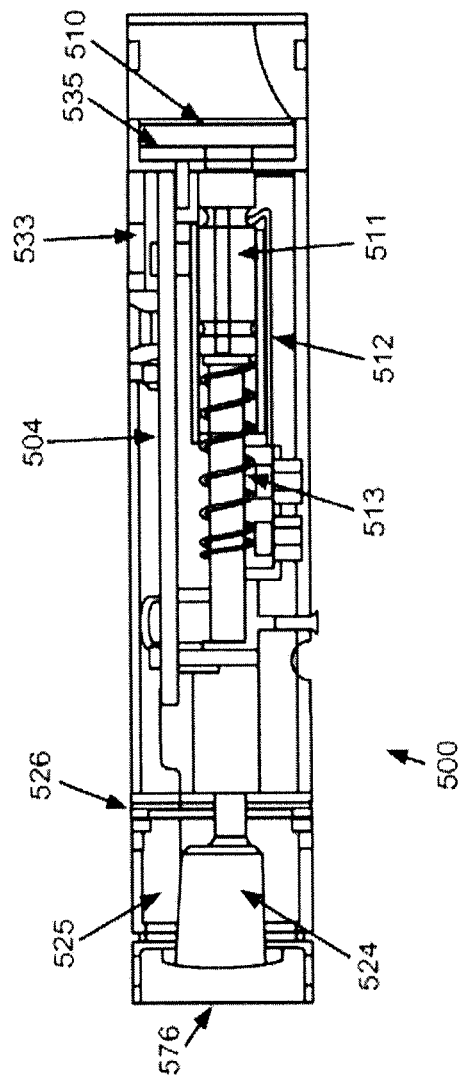
Figure 12:
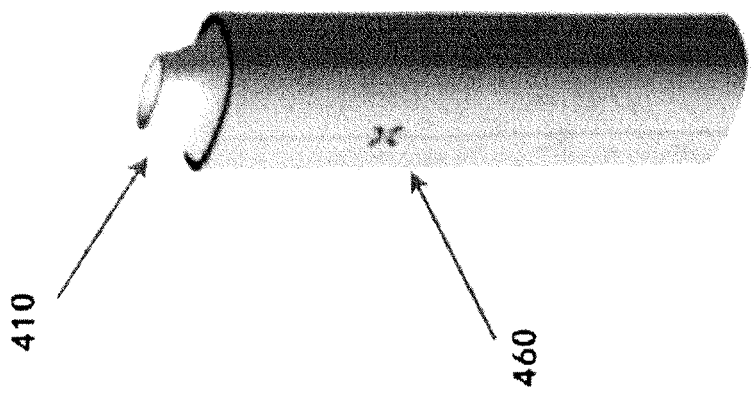
Figure 15:
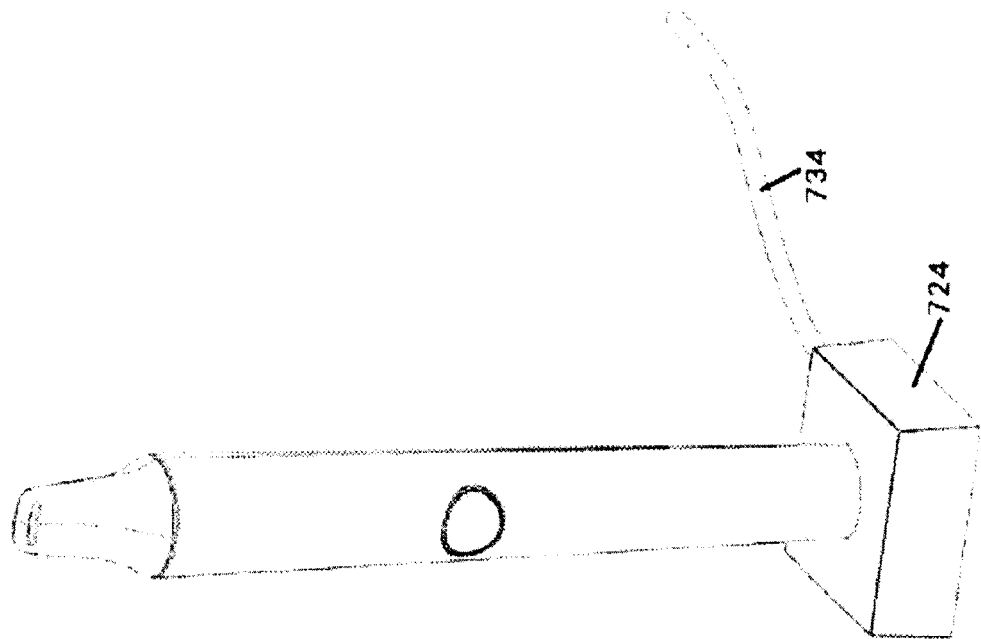
Figure 14:
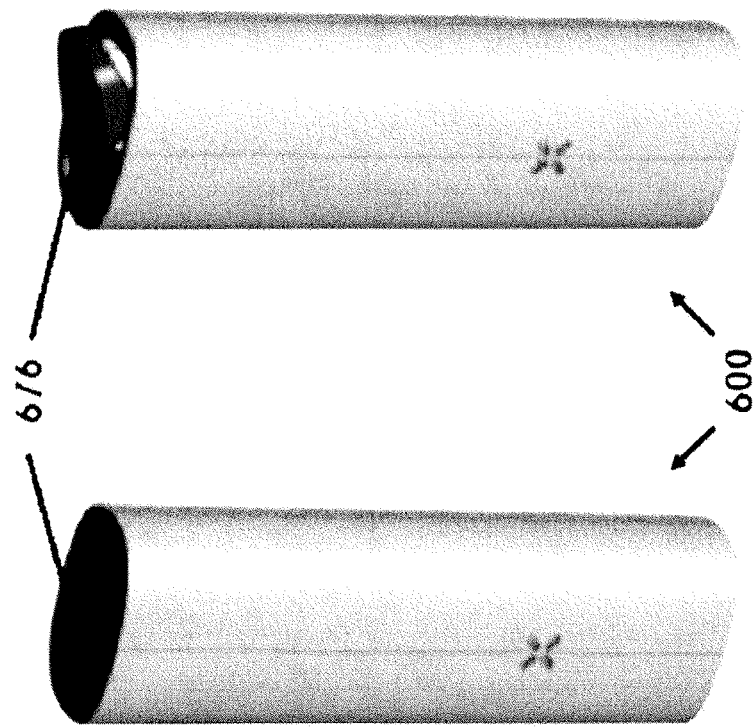
Figure 16:
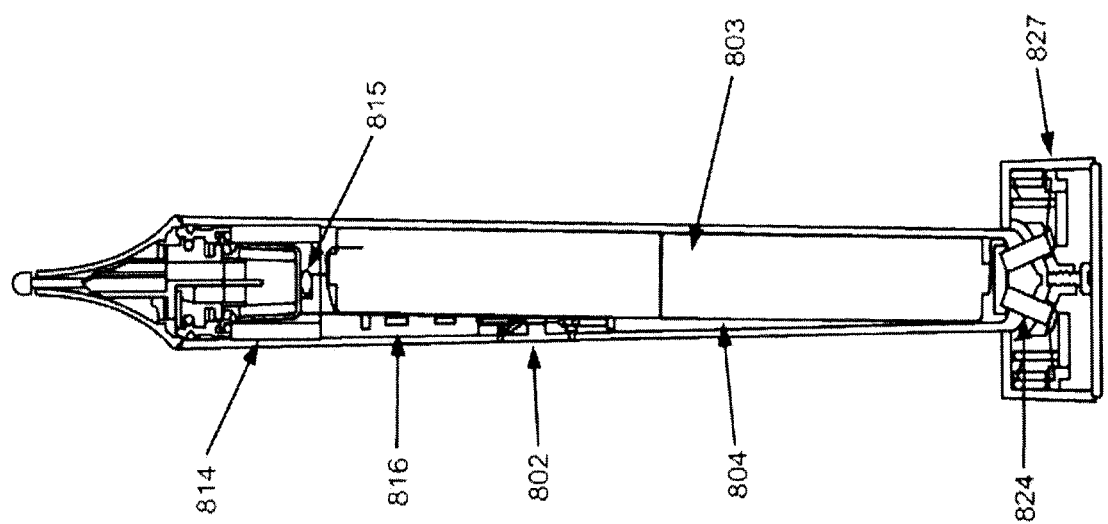

In one embodiment, the tobacco material is a homogenous mixture. In another embodiment, there might be two layers, as shown in FIG. 8. The moist layer 35 has higher content of vapor-forming material than the dry layer 36, which consists of dry tobacco or other material acting as a filter. The dry layer serves to prevent any liquid from bubbling up and out of the cartridge during heating.

In another embodiment of the cartridge, a lower compartment might consist entirely of a vapor-forming medium, such as glycerine. An upper region would consist of the tobacco material to be vaporized, and the two would be separated by a material that only allows the medium to pass in a vapor or gaseous phase. Gore-tex (brand name) is one such material. In use, vapor generated in the lower region would pass through the semi-permeable membrane, volatize the active components of the tobacco, and a mix of the two would be delivered to the user upon inhalation.

In another embodiment, the consistency of the tobacco material is such that the wrapper is not necessary. This is possible if at least the outer surface of the cartridge is dry and cohesive enough to not leave deposits inside the device. Such a cartridge can be made by forming tobacco material in a mold. If the resulting surface is excessively moist, it can be dried by heating the cartridge in an oven.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A portable device for generating an inhalable vapor, the device comprising:
   a cartridge comprising a vaporizable material, the cartridge having one or more receptacles;
   an elongated main body;
   a vaporization chamber disposed within the elongated main body, the vaporization chamber configured to receive the cartridge, the vaporization chamber having an interior bottom surface configured to contact a bottom surface of the cartridge, the interior bottom surface of the vaporization chamber having one or more complementary features relative to the one or more receptacles of the cartridge, wherein the one or more complementary features of the vaporization chamber combined with the one or more receptacles of the cartridge allow for an increase in surface contact therebetween;
   a battery-powered heater disposed within the elongated main body, the battery-powered heater configured to heat the vaporizable material within the vaporization chamber for the generating of the inhalable vapor from the vaporizable material; and
   a microcontroller configured to regulate a temperature of the battery-powered heater.

2. The device of claim 1, wherein the battery-powered heater is separated from the vaporization chamber by a ring made of an insulating medium.

3. The device of claim 1, wherein the device is configured to operate at a temperature below 400° F.

4. The device of claim 1, further comprising a mouthpiece at one end of the main body, the mouthpiece having an inhalation air passage extending therethrough.

5. The device of claim 4, further comprising an air inlet passage between the mouthpiece and the vaporization chamber.

6. The device of claim 4, wherein removal of the mouthpiece exposes the vaporization chamber, and replacement of the mouthpiece closes the vaporization chamber.

7. The device of claim 4, wherein the mouthpiece is thermally insulating to prevent excessive heat from reaching a user's lips.

8. The device of claim 1, further comprising a light emitting diode (LED), wherein the LED is configured to indicate at least one state of the vaporization chamber.

9. The portable device of claim 1, wherein the cartridge comprises a wrapper, and wherein the vaporizable material is disposed within the wrapper.

10. The portable device of claim 1, wherein the microcontroller is configured to regulate a temperature of the battery-powered heater such that a temperature of the vaporization chamber can be maintained at or below 400° F.

11. A portable device for generating an inhalable vapor, the device comprising:
- a cartridge comprising a vaporizable material, the cartridge having one or more receptacles;
- an elongated main body having a tubular casing;
- a vaporization chamber disposed within the tubular casing, the vaporization chamber configured to receive the cartridge, the vaporization chamber having an interior bottom surface configured to contact a bottom surface of the cartridge, the interior bottom surface of the vaporization chamber having one or more complementary features relative to the one or more receptacles of the cartridge, wherein the one or more complementary features of the vaporization chamber combined with the one or more receptacles of the cartridge allow for an increase in surface contact therebetween;
- a battery-powered heater disposed within the tubular casing, the battery-powered heater configured to heat the vaporization chamber for the generating of the inhalable vapor from the vaporizable material; and
- a microcontroller configured to regulate a temperature of the battery-powered heater so that a temperature of the vaporization chamber is less than a prescribed threshold temperature, the prescribed threshold temperature being below 400° F.

12. The portable device of claim 11, wherein the cartridge comprises a wrapper, and wherein the vaporizable material is disposed within the wrapper.

13. The portable device of claim 11, further comprising a light emitting diode (LED), wherein the LED is configured to indicate at least one state of the vaporization chamber.

14. The portable device of claim 13, wherein the at least one state of the vaporization chamber is that the vaporization chamber has reached a prescribed operating temperature.

15. A portable device for generating an-inhalable vapor, the device comprising:
- a cartridge comprising a vaporizable material, the cartridge having one or more receptacles;
- an elongated outer body extending in a longitudinal direction;
- a vaporization chamber disposed within the elongated outer body, wherein the vaporization chamber has a depth in the longitudinal direction that is greater than a width perpendicular to the longitudinal direction, the vaporization chamber configured to receive the cartridge, the vaporization chamber having an interior bottom surface configured to contact a bottom surface of the cartridge, the interior bottom surface having one or more complementary features relative to the one or more receptacles of the cartridge, wherein the one or more complementary features of the vaporization chamber combined with the one or more receptacles of the cartridge allow for an increase in surface contact therebetween;
- a battery-powered heater configured to heat the vaporizable material within the vaporization chamber for the generating of the inhalable vapor from the vaporizable material;
- a battery disposed within the elongated outer body, the battery configured to provide power to the battery-powered heater;
- a microcontroller configured to regulate the temperature of the battery-powered heater; and
- a light-emitting diode configured to at least indicate that the inhalable vapor is ready for consumption.

16. The device of claim 15, wherein the microcontroller is configured-to activate the battery-powered heater to heat the vaporization chamber when a user pushes a button of the device.

17. The device of claim 15, wherein the battery-powered heater is configured for rapid heating, and the vaporization chamber comprises a thin-walled elongate tube.

18. The portable device of claim 15, wherein the cartridge comprises a wrapper, and wherein the vaporizable material is disposed within the wrapper.

* * * * *